US010682182B2

(12) United States Patent
Hogan et al.

(10) Patent No.: US 10,682,182 B2
(45) Date of Patent: Jun. 16, 2020

(54) CONFIGURING A SURGICAL TOOL

(71) Applicant: 360 Knee Systems Pty Ltd, New South Wales (AU)

(72) Inventors: Jason Hogan, New South Wales (AU); Brad Peter Miles, New South Wales (AU); Peter Bede O'Connor, New South Wales (AU); Stephen McMahon, New South Wales (AU)

(73) Assignee: 360 KNEE SYSTEMS PTY LTD., New South Wales (AU)

( * ) Notice: Subject to any disclaimer, the term of this patent is extended or adjusted under 35 U.S.C. 154(b) by 149 days.

(21) Appl. No.: 15/744,410

(22) PCT Filed: Jul. 14, 2016

(86) PCT No.: PCT/AU2016/050617
§ 371 (c)(1),
(2) Date: Jan. 12, 2018

(87) PCT Pub. No.: WO2017/008119
PCT Pub. Date: Jan. 19, 2017

(65) Prior Publication Data
US 2018/0199996 A1 Jul. 19, 2018

(30) Foreign Application Priority Data
Jul. 15, 2015 (AU) .............................. 2015902806

(51) Int. Cl.
*A61B 34/10* (2016.01)
(52) U.S. Cl.
CPC ........ *A61B 34/10* (2016.02); *A61B 2034/102* (2016.02); *A61B 2034/104* (2016.02); *A61B 2034/105* (2016.02)

(58) Field of Classification Search
CPC ..... A61B 17/15; A61B 17/151; A61B 17/155; A61B 17/157; A61B 17/1703;
(Continued)

(56) References Cited
U.S. PATENT DOCUMENTS
2001/0036245 A1 11/2001 Kienzle, III et al.
2005/0216032 A1 9/2005 Hayden
(Continued)

FOREIGN PATENT DOCUMENTS
EP 2 835 105 A1 2/2015

OTHER PUBLICATIONS
"International Search Report" issued in PCT/AU2016/050617, dated Sep. 20, 2016, 4 pages.
(Continued)

Primary Examiner — Eric S Gibson
(74) Attorney, Agent, or Firm — Kilpatrick Townsend & Stockton LLP

(57) ABSTRACT

The present disclosure relates to a method and system for configuring a surgical tool during surgery. A laser scanner generates sensor data and a processor determines spatial data indicative of a position of the anatomical feature and of a position of a tool interface that is fixed in relation to the anatomical feature based on the sensor data. The processor also determines a first desired spatial configuration of the surgical tool in relation to the tool interface based on the spatial data and a second desired spatial configuration of the surgical tool in relation to the anatomical feature. The outcome is more accurate and less complex than other methods, such as methods that are based on reference to the absolute positions of the anatomical feature and the surgical tool within an operation theatre.

22 Claims, 19 Drawing Sheets

(58) Field of Classification Search
CPC .............. A61B 34/10; A61B 2034/102; A61B 2034/104; A61B 2034/105
See application file for complete search history.

(56) References Cited

U.S. PATENT DOCUMENTS

| | | |
|---|---|---|
| 2011/0130761 A1 | 6/2011 | Plaskos et al. |
| 2012/0071893 A1 | 3/2012 | Smith et al. |
| 2013/0060278 A1 | 3/2013 | Bozung et al. |
| 2014/0107471 A1* | 4/2014 | Haider ............... A61B 17/1703 600/424 |
| 2016/0022374 A1* | 1/2016 | Haider .................. A61B 17/17 606/96 |
| 2017/0312031 A1* | 11/2017 | Amanatullah ......... A61B 17/16 |
| 2017/0312032 A1* | 11/2017 | Amanatullah ......... A61B 34/10 |
| 2018/0199996 A1* | 7/2018 | Hogan .................. A61B 34/10 |
| 2018/0325618 A1* | 11/2018 | Justin ..................... A61B 90/37 |

OTHER PUBLICATIONS

"International Preliminary Report on Patentability", issued in PCT/AU2016/050617, dated Jul. 18, 2017, 4 pages.

* cited by examiner

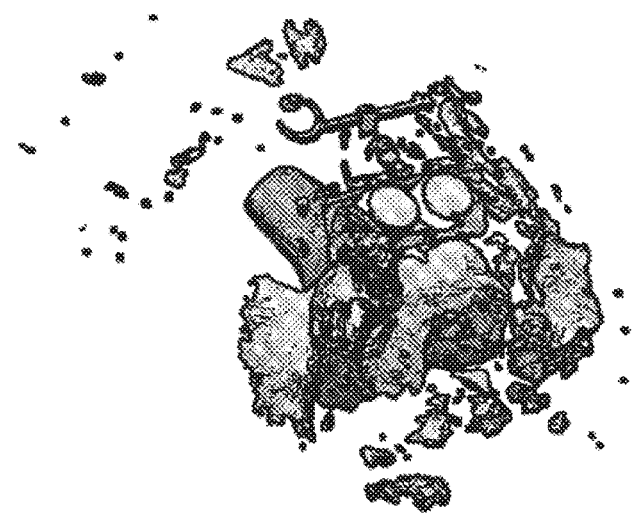
Fig. 4(l)
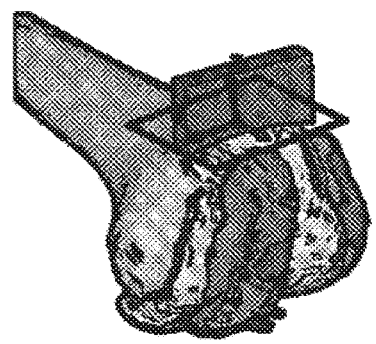
Fig. 4(m)
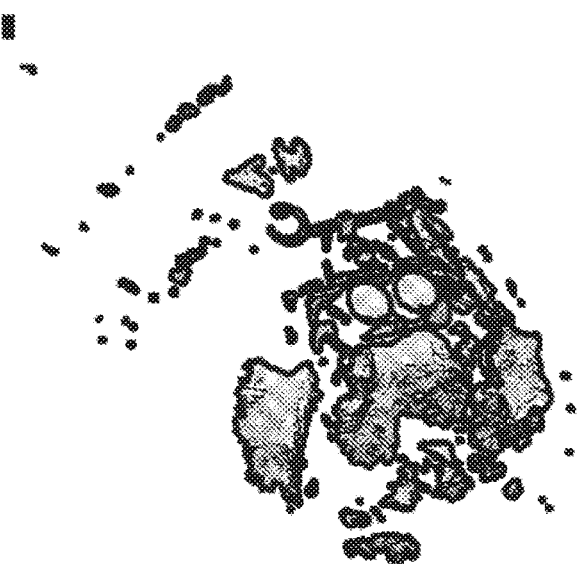
Fig. 4(n)
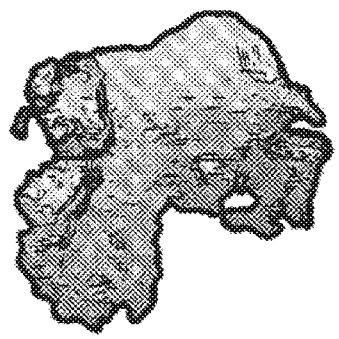
Fig. 4(o)
Fig. 8

```
        publicstaticvoid ExtractRotationsFrom4x4Matrix(Matrix3D
matrix, outdouble rfYAngle, outdouble rfPAngle, outdouble rfRAngle)
        {
                rfPAngle =  Math.Asin(-matrix.M23 );

if (rfPAngle <Math.PI *0.5)
                {
                    if (rfPAngle >-Math.PI *0.5)
                    {
                        rfYAngle =Math.Atan2 (matrix.M13 , matrix.M33 );
                        rfRAngle =Math.Atan2 (matrix.M21, matrix.M22);
                        return;
                    }
                    else
                    {
                        double fRmY =Math.Atan2(-matrix.M12, matrix.M11);
                        rfRAngle =   (0f);
                        rfYAngle = rfRAngle - fRmY;
                        return;
                    }
                }

}
```
Fig. 10(a)

```
privateTransform3D gettransformfrom3points(Point3DCollection
points)
        {
                if (points.Count !=3)   returnTransform3D.Identity ;
                Vector3D V1 = points[0] - points[1];
                Point3D Mid =newPoint3D(
                    (p1.X + p2.X) *0.5,
                    (p1.Y + p2.Y) *0.5,
                    (p1.Z + p2.Z) *0.5);
                V1.Normalize();
                Vector3D V2 = Mid - points[2];
                Point3D Origin =newPoint3D(
                    (p1.X + p2.X) *0.5,
                    (p1.Y + p2.Y) *0.5,
                    (p1.Z + p2.Z) *0.5);
  Vector3D V3 =Vector3D.CrossProduct(V1, V2);
                V3.Normalize();
                V2 =Vector3D.CrossProduct(V1, V3);

return    Matrix3D mat =newMatrix3D(V1.X, V1.Y, V1.Z, 0,
   V2.X, V2.Y, V2.Z, 0, V3.X, V3.Y, V3.Z, 0, Origin.X, Origin.Y,
   Origing.Z, 1);
        }
```
Fig. 10(b)

$$1102 \quad E(a, b, r) = \sum_{i=1}^{m}(L_i - r)^2$$

$$1104 \quad \frac{\partial E}{\partial r} = -2\sum_{i=1}^{m}(L_i - r).$$

$$1106 \quad r = \frac{1}{m}\sum_{i=1}^{m} L_i.$$

$$1108 \quad \frac{\partial E}{\partial a} = -2\sum_{i=1}^{m}(L_i - r)\frac{\partial L_i}{\partial a} = 2\sum_{i=1}^{m}\left((x_i - a) + r\frac{\partial L_i}{\partial a}\right)$$

$$1110 \quad \frac{\partial E}{\partial b} = -2\sum_{i=1}^{m}(L_i - r)\frac{\partial L_i}{\partial b} = 2\sum_{i=1}^{m}\left((y_i - b) + r\frac{\partial L_i}{\partial b}\right)$$

$$1112 \quad \frac{\partial E}{\partial c} = -2\sum_{i=1}^{m}(L_i - r)\frac{\partial L_i}{\partial c} = 2\sum_{i=1}^{m}\left((z_i - c) + r\frac{\partial L_i}{\partial c}\right)$$

$$1114 \quad a = \frac{1}{m}\sum_{i=1}^{m} x_i + r\frac{1}{m}\sum_{i=1}^{m}\frac{\partial L_i}{\partial a}$$

$$1116 \quad b = \frac{1}{m}\sum_{i=1}^{m} y_i + r\frac{1}{m}\sum_{i=1}^{m}\frac{\partial L_i}{\partial b}.$$

$$1118 \quad c = \frac{1}{m}\sum_{i=1}^{m} z_i + r\frac{1}{m}\sum_{i=1}^{m}\frac{\partial L_i}{\partial c}.$$

Fig. 11

$$1202 \rightarrow a = \bar{x} + \bar{L}\bar{L}_a =: F(a, b, c)$$

$$1204 \rightarrow b = \bar{y} + \bar{L}\bar{L}_b =: G(a, b, c)$$

$$1206 \rightarrow c = \bar{z} + \bar{L}\bar{L}_c =: H(a, b, c)$$

$$1208 \begin{cases} \bar{x} = \frac{1}{m} \sum_{i=1}^{m} x_i \\ \bar{y} = \frac{1}{m} \sum_{i=1}^{m} y_i \\ \bar{z} = \frac{1}{m} \sum_{i=1}^{m} z_i \\ \bar{L} = \frac{1}{m} \sum_{i=1}^{m} L_i \\ \bar{L}_a = \frac{1}{m} \sum_{i=1}^{m} \frac{a - x_i}{L_i} \\ \bar{L}_b = \frac{1}{m} \sum_{i=1}^{m} \frac{b - y_i}{L_i} \\ \bar{L}_c = \frac{1}{m} \sum_{i=1}^{m} \frac{c - z_i}{L_i} \end{cases}$$

Fig. 12

$$c_x = x - r\cos\theta\sin\varphi$$
$$c_y = y - r\sin\theta\sin\varphi$$
$$c_z = z - r\cos\varphi$$

--- for *for every point (x, y, z)* do
    for $(r = r_{min}; r \leq r_{max}; r++)$ do
        for $\theta = 0; \theta \leq 2\pi; \theta++$ do
            for $\varphi = 0; \varphi \leq \pi; \varphi++$ do
                $c_x = x - r\cos\theta\sin\varphi$
                $c_y = y - r\sin\theta\sin\varphi$
                $c_z = z - r\cos\varphi$
                Accumulator$[r][c_x][c_y][c_z]$++
            end
        end
    end
end
Search Accumulator for peak.

Fig. 13

```
function ICP(Scene,Model)
 begin
  E` = + ∞;
  (Rot,Trans) = InInitialize-Alignment(Scene,Model);
  repeat
E = E`;
Aligned-Scene = Apply-Alignment(Scene,Rot,Trans);
Pairs = Return-Closest-Pairs(Aligned-Scene,Model);
(Rot,Trans,E`) = Update-Alignment(Scene,Model,Pairs,Rot,Trans);
  Until |E`- E|  < Threshold
  return (Rot,Trans);
end
```

Fig. 14

CONFIGURING A SURGICAL TOOL

CROSS-REFERENCE TO RELATED APPLICATIONS

The present application is a U.S. National Stage of International Application No. PCT/AU2016/050617 filed on Jul. 14, 2016, which claims priority from Australian Provisional Patent Application No 2015902806 filed on 15 Jul. 2015. Each of these applications is hereby incorporated herein by reference in its entirety for all purposes.

TECHNICAL FIELD

The present disclosure relates to a method and system for configuring a surgical tool during surgery.

BACKGROUND

It is important to accurately position surgical tools during surgery to allow the most effective treatment. One example includes surgery in relation to bones and joints, such as knee and hip replacement surgery. This may involve cutting, or otherwise shaping, bone and cartilage of the patient and securing implantable components thereto.

This requires the surgical tools to be accurately configured relative to the patient such that the surgical tool can operate in accordance with the surgical plan. This may involve apparatus and systems that assist the surgeon to guide the surgical tool to the desired position.

As an example, a positioning guide may be placed relative to anatomical features of the patient. Anatomical features may include portions of the surface of the bone, cartilage and soft tissue constructs. The surgeon may then position surgical tools relative to the positioning guide. The positioning guide may then assist a blade to cut the bone, assist drilling into the bone, assist insertion of pins into the bone, and/or assist positioning and securing an implant to the bone. However, a positioning guide needs to be made for a specific patient before surgery and may be limited to guiding a single surgical tool to a single configuration.

An alternative may be a re-usable instrument with settings that are not patient specific, such as an intramedullary rod to reference distance femoral cut on the femur.

Therefore, such known methods and systems for configuring surgical tools would require the desired configuration of the surgical tool known in advance of surgery so that a positioning guide may be manufactured. This reduces the flexibility, such as in cases where the desired configuration may not be known until shortly before surgery.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion any other element, integer or step, or group of elements, integers or steps.

In the present description the term "position" reference to a position of an element may include a position of the element in two, or three, dimensional space and may also include the orientation of the element.

SUMMARY

A method for configuring a surgical tool in relation to an anatomical feature, the method comprising:

determining spatial data indicative of a position of the anatomical feature and of a position a reference feature that is fixed in relation to the anatomical feature; and determining a first desired spatial configuration of the surgical tool in relation to reference feature based on;

the spatial data, and a second desired spatial configuration of the surgical tool in relation to the anatomical feature. Since the method determines a desired spatial configuration that is in relation to the reference feature and the reference feature is fixed to the anatomical feature, the outcome may be more accurate and less complex than other methods, such as methods that are based on reference to the absolute positions of the anatomical feature and the surgical tool within an operation theatre.

Determining the spatial data indicative of a position of the anatomical feature and of a position of a reference feature may comprise determining spatial data indicative of a position of the anatomical feature and of a position of a tool interface.

Determining the spatial data indicative of a position of the anatomical feature and of a position of a reference feature may comprise determining spatial data indicative of a position of the anatomical feature and of a position of one or more of: a cartilage defect and a bone feature. The bone feature may be a medial epicondyle.

In the method, the second desired spatial configuration in relation to the anatomical feature may be based on a dynamic anatomical model.

In the method, the second desired spatial configuration in relation to the anatomical feature may be further based on a dynamic simulation of the dynamic anatomical model.

In the method, the anatomical feature may be a model feature of the dynamic anatomical model.

In the method, the second desired spatial configuration in relation to the anatomical feature may be based on an anatomical model. The anatomical model may be a 3D mesh model.

In the method, determining the first spatial configuration may comprise aligning the anatomical model with the spatial data. In the method, aligning the anatomical model with the spatial data may be based on a default position of the reference feature. In the method, aligning the anatomical model with the spatial data may comprise determining areas of the spatial data which are inaccurate and discarding the inaccurate areas from the alignment. In the method, aligning the anatomical model with the spatial data may comprise determining areas of the spatial data which are highly accurate and aligning the anatomical model with the spatial data based on the highly accurate areas.

In the method, aligning the anatomical model with the spatial data may comprise morphing the anatomical model.

In the method, determining spatial data indicative of the position of the tool interface may comprise determining spatial data indicative of the position of a marker engaged with the tool interface.

In the method, determining spatial data may comprise determining spatial data that is indicative of the position of the anatomical feature relative to the tool interface.

In the method, determining the spatial data may comprise determining the spatial data based on range finder data. Determining the spatial data may comprise determining for multiple points a distance from a sensor position.

In the method, the anatomical feature may comprise a feature of a bone. The feature of the bone may comprise a feature of a bone within a human knee.

The method may comprise determining the second desired spatial configuration based on an anatomical model and medical imaging data.

The surgical tool may be a bone-preparation tool and the determining the first desired spatial configuration may comprise determining a first preparation angle in relation to the tool interface and the second desired spatial configuration comprises a second preparation angle in relation to the bone. Bone preparation may comprise one or more of cutting, drilling, reaming, machining, shaving and fracturing.

In the method, the second desired spatial configuration of the surgical tool may comprise a desired geometry of the anatomical feature after applying the surgical tool.

The method may further comprise generating an output signal to set the surgical tool to the first desired spatial configuration.

The method may further comprise performing the step of determining the spatial data at another time to determine a result of applying the surgical tool.

In the method, determining the result of applying the surgical tool may comprise determining a position of an implant in relation to the anatomical feature.

In the method, determining the result of applying the surgical tool may comprise determining a position of a marker.

Software that, when installed on a computer, causes the computer to perform the method described above.

A system for configuring a surgical tool in relation to an anatomical feature, the system comprising:
an input port to receive sensor data;
a processor
to determine based on the sensor data spatial data indicative of a position of the anatomical feature and of a position of a tool interface that is fixed in relation to the anatomical feature; and
to determine a first desired spatial configuration of the surgical tool in relation to the tool interface based on the spatial data and a second desired spatial configuration of the surgical tool in relation to the anatomical feature.

The system may further comprise a laser range finder to generate the sensor data and communicatively coupled to the input port.

BRIEF DESCRIPTION OF DRAWINGS

Examples of the present disclosure will be described with reference to:

FIGS. 4(l) and 4(m) illustrate how the scan and targets, respectively, are transformed relative to the default array position;

FIG. 4(n) shows an example of 21,000 nodes of the scan;

FIG. 4(o) shows an example of 3,500 nodes of the 3D mesh model.

FIG. 10a illustrates example code for the determination of the rotation angle.

FIG. 10b illustrates example code for creating a transformation from three spheres.

FIG. 11 illustrates steps of a method for fitting a sphere to 3D Points.

FIG. 12 illustrates three non-linear equations with according parameter expressions.

FIG. 13 illustrates an example method for sphere detection within the point cloud.

FIG. 14 illustrates example code for iterative closest point calculation.

DESCRIPTION OF EMBODIMENTS

Overview

Figure 1:
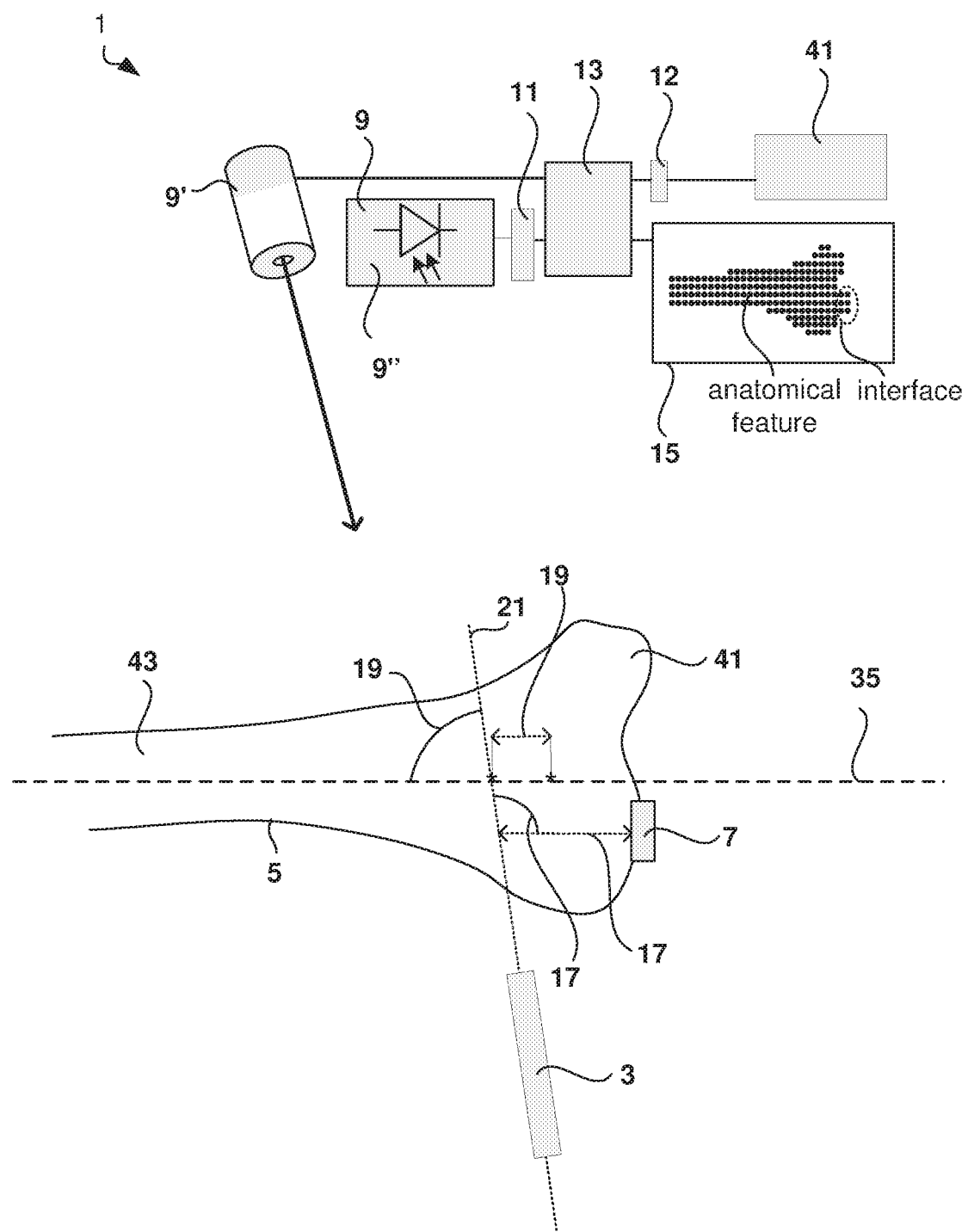
FIG. 1 is a schematic view of a system for configuring a surgical tool relation to an anatomical feature.

FIG. 1 illustrates a system 1 for configuring a surgical tool 3 in relation to an anatomical feature 5, where a reference feature, in this example a tool interface 7, is fixed in relation to the anatomical feature 5. A sensor system 9 detects the anatomical feature 5 and the tool interface 7, which in turn sends sensor data to be received by an input port 11 of the system 1.

The system 1 includes a processing device 13 having a processor to determine spatial data 15 indicative of a position of the anatomical feature 5 and a position of the tool interface 7 based on the received sensor data. The processing device 13 also determines a first desired spatial configuration 17 of the surgical tool 3 in relation to the tool interface 7 based on the spatial data 15 and a second desired spatial configuration 19 of the surgical tool 3 in relation to the anatomical feature 5. The processing device 13 may send an output signed via output port 12 to a surgical tool apparatus 47 that positions the surgical tool 3.

There is also disclosed a method 200 of configuring a surgical tool 3 in relation to an anatomical feature 5. The method 200 may be performed by a processor of the processing device 13 and includes determining 210 spatial data 15 indicative of a position of the anatomical feature 5 and a position of the tool interface 7. The method 200 further includes determining 220 a first desired spatial configuration of the surgical tool 3 in relation to the tool interface 7. The first desired spatial configuration may be based on the spatial data (representative of positions of the anatomical feature 5 and the tool interface 7) and a second desired spatial configuration of the surgical tool in relation to the anatomical feature.

Since the method determines the first desired spatial configuration in relation to the tool interface 7, and the tool interface is fixed to the anatomical feature 5, the result may be more accurate and less complex than other methods. For example, the disclosed method 200 may be more accurate that methods that are based on determinations of absolute positions of the anatomical feature 5 within an operation theatre and positioning the surgical tool 3 with reference to the absolute position of the surgical tool 3 in the operation theatre.

While some examples in this disclosure relate to determining the position of the tool interface 7, it is to be understood that equally and more generally, processing device 13 may determine spatial data 15 indicative of a position of the anatomical feature 5 and a position of a reference feature, such as a cartilage defect or a bone feature, such as a medial epicondyle. The reference feature is also fixed in relation to the anatomical feature 5 and may be a pre-defined fixed reference feature, such as a bone feature or patient specific cartilage defect selected by an operator, doctor or surgeon.

Description of an Embodiment of the Method

An example of a process of replacing a joint of a patient using the method 200 and system 1 will now be described. This includes surgery planning followed by a surgery where the method 200 is employed.

Surgery Planning and Determining a Desired Spatial Configuration of the Surgical Tool in Relation to the Anatomical Features 205

Figure 3:
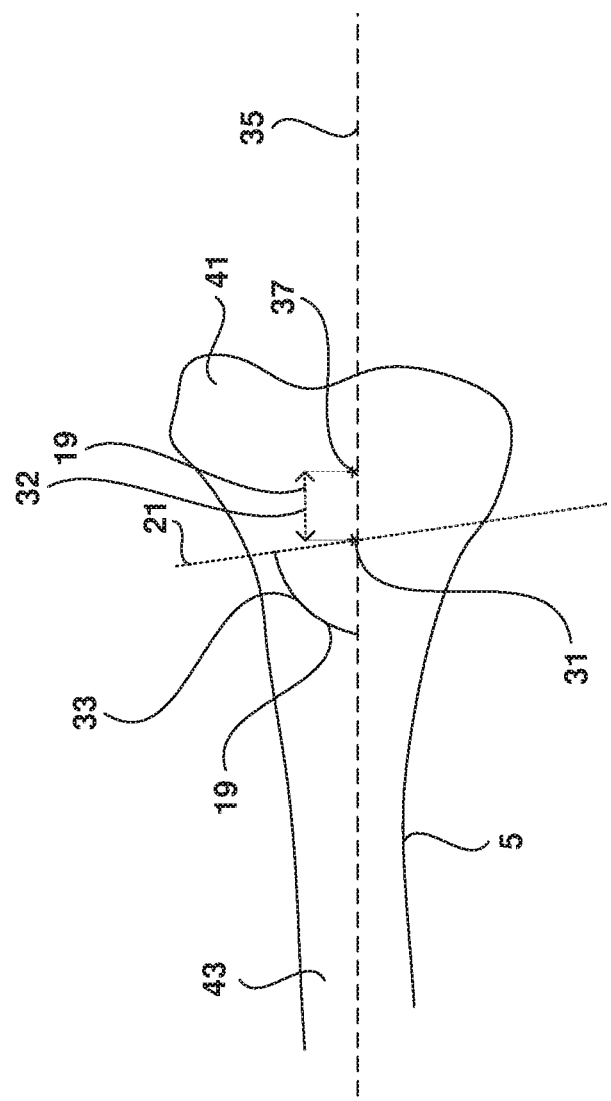
FIG. 3 illustrates a side view of an anatomical feature and a proposed cut line.
Figure 6:
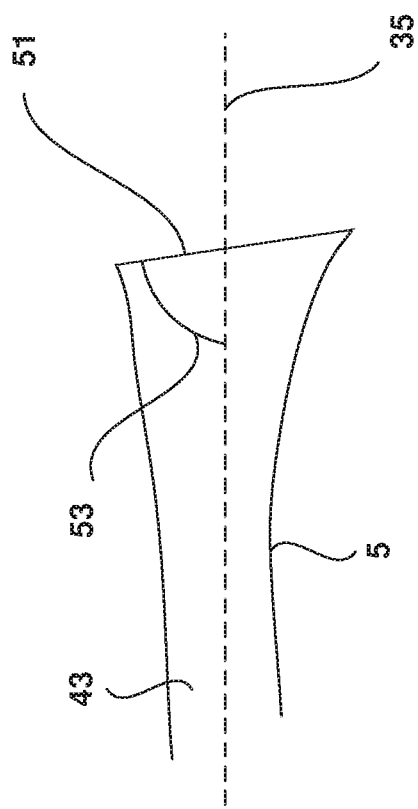
FIG. 6 illustrates a side view of a shaped portion of the anatomical feature after applying the surgical tool.
Figure 7:
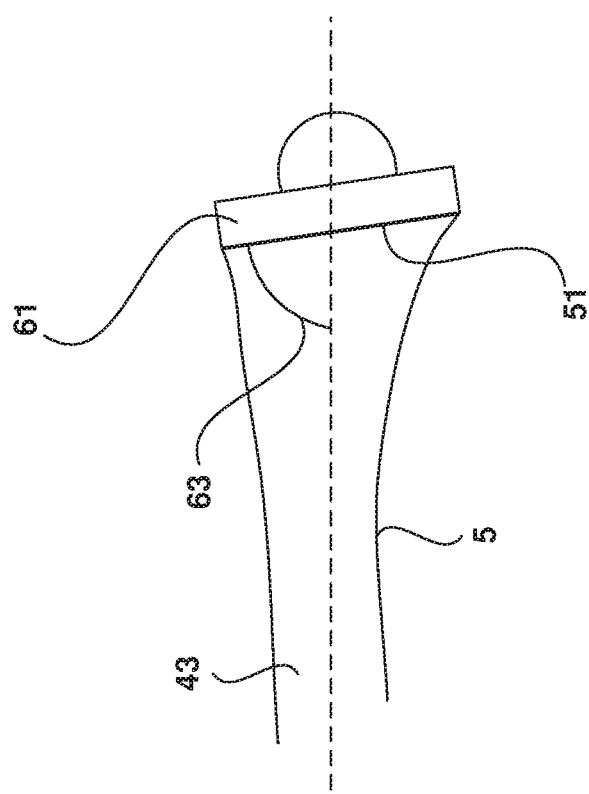
FIG. 7 illustrates a side view of the anatomical feature with an implant.

A surgical plan may include shaping the anatomical feature 5 so that it is suitable for receiving an implant 61. Importantly, the result of shaping of the anatomical feature 5 should be relative to the anatomical feature 5. FIG. 3 illustrates an example of proposed shaping of the anatomical feature 5 to achieve a desired geometry (which in this case is shaping an end portion of a femur bone). The proposed shaping includes cutting the bone 5 along line 21 (which may be representative of a plane in three dimensions) to provide a shaped anatomical feature 5 as illustrated in FIG. 6. After proposed cutting, and any other preparation work to achieve the desired geometry, the anatomical feature 5 may receive an implant 61 such as parts of an artificial joint as illustrated in FIG. 7.

To improve the likelihood of successful surgery, it is desirable to have an accurately defined cut line 21 or plane relative to the anatomical features 5. The cut line 21 or cutting plane may correspond to the desired shaped surfaces of the anatomical feature 5. It is to be appreciated that in some examples, this may involve multiple cut lines 21 or planes and may further include limitations on how the cut is made, such as the length, the orientation, the type of tool, etc.

In the example of FIG. 3, the cut line 21 may corresponds to the desired shape of the anatomical feature 5 (or an offset thereof). Furthermore, the cut line 21 corresponds to the desired path for the surgical tool 3 (or an offset thereof). That is, to achieve the desired shape for the anatomical feature 5, the surgical tool 3 should be configured at relative to the anatomical feature 5 so that the working portion of the surgical tool 3 is on (or movable along) the cut line 21. This is illustrated in this example with the second desired spatial configuration 19 of the surgical tool 3 relative to the anatomical feature 5 that includes a position 31 (at a displacement 32 from a reference location 37 of the anatomical feature 5) and a second cutting angle 33 (from a reference axis 35) that corresponds to the cut line 21.

It is to be appreciated that the second desired spatial configuration 19 of the surgical tool 3 may be expressed in a variety of ways. For example, defining the cut line 21 may include specifying an angle and one position (of an infinite number) that falls on the line. Alternatively, the line 21 may be defined by specifying two positions, where the line 21 is determined as a straight line that passes through the two specified positions. In another example, the second desired spatial configuration may include a plane, which is defined by specifying three positions that the plane passes through. It is also to be appreciated difference coordinate systems may be used, such as polar coordinates, Cartesian coordinates, etc.

Determining 205 the second desired spatial configuration 19 may be performed during the planning stages of the surgery. As noted above, the second desired spatial configuration 19 is generally dictated by the desired resultant shape of the anatomical feature 5. The desired shape of the anatomical feature 5, in turn depends on a variety of factors including the type and shape of the implant 61, the physiological characteristics of the patient, and other characteristics of the patient. Other characteristics of the patient may include the types of physical activity that the patient is likely to perform, such a running, playing golf, etc.

In one example, the implant (such as a replacement joint) may be tailored to a patient's other characteristics. For example, a person who is expected to have high levels of walking, jogging or even running, may have a particular replacement joint that is suitable for his or her needs. This may also include having a desired shape of the anatomical feature 5 that would be suitable for the particular replacement joint and/or the expected level of activity.

The present system 1 and method 200 may be suitable for replacement surgery with personalised orthopaedics. Such personalised orthopaedics may include treatment involving dynamic anatomic models and simulations thereof. In these systems, personal anatomic information of a patient is collected, such as those derived from medical imaging data such as CT scan (X-ray computed tomography) or MRI (magnetic resonance imaging). The information is then sent to a processor to build three dimensional computer models of the individual's joint. The computer models that are used may undergo dynamic simulations of the joint. This may include simulations with normal activities, such as walking, standing and sitting. It may also include dynamic simulations that may be characteristic of the patient, for example a patient who plays golf or tennis. Such simulations may allow identification of particular stresses and wear on the anatomy or type of implant. It may also allow simulation of other performance characteristics of the joint as well as assisting optimisation of the joint. The simulation may therefore assist in developing a tailored artificial joint for the patient, which may determine 205 a particular second spatial configuration 19 for the surgical tool 3 in relation to the anatomical features 5.

Examples of dynamic anatomical models include the Optimized Ortho hip product called Corin OPS (Corin Optimized Positioning System) those described in International Publication Numbers WO 2012/113030 (PCT/AU2012/000179) in the name of Optimized Ortho Pty Ltd, the contents of which are hereby incorporated by reference. An example of a knee product is PREKS (Pre-Operative Knee Analysis Report). A feature of the PREKS Report is the DKS (Dynamic Knee Score).

After determining the second desired spatial configuration for the surgical tool 3 in relation to the anatomical feature 5, the surgeon may proceed with performing surgery. However, in known systems there may be difficulties in configuring a surgical tool 3 with direct relation to an anatomical feature 5, or using the anatomical feature 5 directly as a reference or indexing surface. For example, the anatomical feature 5 may be obscured by other tissue making it difficult to observe the anatomical feature 5 and use it as a point of reference. The present system 1 and method 200 may ameliorate these difficulties by providing an alternative reference to the surgical tool 3.

Determining Spatial Data Indicative of a Position of the Anatomical Feature and a Position of a Tool Interface 210

In surgery, tissue may be cut so that part of the anatomical feature 5 is exposed. A tool interface 7 is then fixed in relation to the anatomical feature 5 of the patient. The tool interface 7 may, for example, include a pin or screw that is secured to the anatomical feature 5. This may be facilitated by a surgeon drilling into the anatomical feature 5 to receive fasteners fixing the tool interface 7. Referring to the example in FIG. 4(*a*), the tool interface 7 is fixed to a minor portion 41 of the anatomical feature 5 that will be cut off a main portion 43 of the anatomical feature 5. That is, the minor portion 41 will be discarded after the surgery and therefore drilling or otherwise securing the tool interface 7 into the minor portion 41 may not affect the remaining main portion 43 of the anatomical feature 5.

After the tool interface 7 is fixed to the anatomical feature 5, the respective positions of the tool interface 7 and anatomical features 5 are determined 210. This may be important as the actual position (including orientation) may be different to the intended position for the tool interface 7 that the surgeon had planned. For example, it may be difficult for a surgeon to precisely position and fix the tool interface 7 to the minor portion 41. Factors such as obstruction by other human tissue, inaccuracies in tools, errors caused by human factors of the surgeon, etc. may result in the surgeon positioning the tool interface 7 at a position that was not originally intended during surgery planning. Alternatively, the surgeon may discover during surgery that there is damage to parts of the anatomical feature 5 where the tool interface was planned to be fixed. As a consequence the tool interface 7 had to be fixed to another position on the anatomical feature 5.

To determine 210 spatial data that is indicative of the position of the anatomical feature 5 and the position of the tool interface 7, the sensor system 9 performs a scan of the anatomical feature 5 and tool interface 7 as shown in FIG. 1. The sensor system 9 sends the respective sensor data to be received by the input port 11.

In some examples, the spatial data may include at least part of the sensor data. In other forms, the sensor data is used to determine the spatial data. Spatial data may include may forms, and in one example sensor data from the scan may be represented by a 3D point cloud showing spatial information of the detected area of the sensor system 9.

Figure 4A:
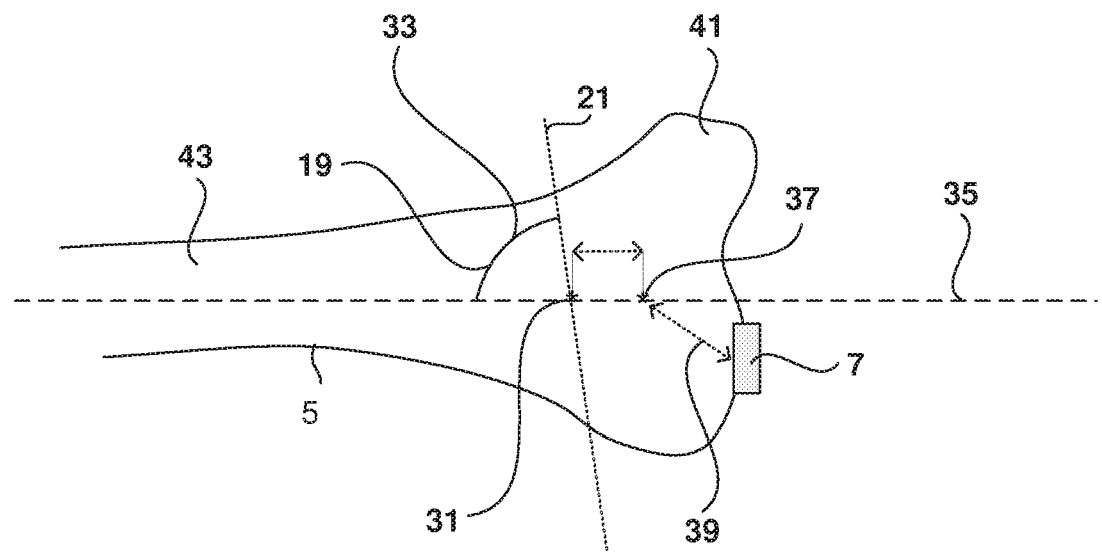
FIG. 4(a) illustrates a side view of an anatomical feature with a fixed tool interface.

FIG. 4(*b*) shows a representation of a 3D point cloud generated from sensor data received from the sensor system 9 that scanned the anatomical feature 5 and tool interface shown in FIG. 4*a*. From the 3D point cloud, the position of the anatomical features 5 and the tool interface 7 may be determined. In one example, a feature extraction algorithm may be used to determine the anatomical feature 5 and the tool interface 7 in the 3D point cloud. Once these are identified, the respective positions of the anatomical feature (such as position of reference position 37) and the tool interface 7 may be determined.

In another example, processor 102 determines the position of the anatomical features 5 based on medical imaging data, such as CT or MRI images. Processor 102 analyses the medical imaging data and constructs a 3D segmented mesh that represents the imaging data. However, the reference feature 7 is applied during surgery, that is, after the medical imaging has been performed. As a result, the reference feature 7 is not visible in the medical imaging. The aim is to use the medical imaging and the derived 3D mesh model as an accurate representation of the anatomical features and then use the surface laser scan to align the actual anatomical features in front of the surgeon with the model. Since the reference feature 7 is now applied, this alignment step can provide the relative position of the reference feature in the 3D mesh model. In other words processor 102 determines the scanned position of the reference feature, such as an alignment array or other reference tool by calculating a best fit convergence between the points within the laser scan and the points generated within the 3D segmented mesh (derived from the medical images).

FIG. 4(*c*) illustrates a 3D mesh model 401 to assist with the best fit convergence the 3D segmented mesh is post processed using the following techniques.

In one example, there is a default position defined for the reference array and the processor 102 performs the following steps:

The approximate default location of the reference block is determined by detecting the distal condyle contact points 402 and 403.

The derived contact points are used to generate an offset plane 404.

The plane is intersected with the mesh geometry 401.

A transformation matrix is created from the anterior region of the intersection curves 405 and 406 (this determines the location of the array block 407).

The transformation matrix may have the following form:

$$\begin{bmatrix} LoXx & LoXy & LoXz & 0 \\ LoYx & LoYy & LoYz & 0 \\ LoZx & LoZy & LoZz & 0 \\ LoOx & LoOy & LoOz & 1 \end{bmatrix}$$

One aspect that may reduce the accuracy of alignment between the 3D mesh model from the medical imaging and the surface scan may be the presence of soft tissue on the bone 401. While the bone is accurately represented by a CT image, the soft tissue is transparent to X-Ray waves and therefore causes little to no effect in the CT image. However, the soft tissue does reflect the laser beam 9' which may result in a discrepancy between the laser scan and the 3D mesh model. In other words, the different wavelengths of radiation used for creating the 3D mesh model and for generating the surface scan may lead to different kinds of tissues being imaged and included.

In order to increase the accuracy of the alignment, processor 102 may exclude regions of the 3D mesh model from the alignment process. There are regions with both the distal femur and proximal tibia where soft tissue is most likely to be present, examples of which include the tibia spline. FIG. 4d illustrates an example area 403 in the PCL attachment that is excluded from the alignment process.

These areas can be identified within the 3D segmented mesh and tagged to be included or excluded during the alignment process. FIG. 4(d) shows a graphical representation of the tags within the distal femur where the faces around the pcl attachment have be tagged to exclude (non-confident or potentially inaccurate regions) and the areas around the distal and anterior regions including osteophytes have been tagged to include (confident or potentially highly accurate regions). Processor 102 may perform the alignment only on the confident regions or only on the regions that have not been excluded. Processor 102 may also apply a small weighting factor to non-confident regions (which could be zero) and/or a large weighting factor to confident regions.

Processor 102 may create a number of morphed surrogate model in order to enhance the alignment process when using CT images. The morphed models may be created using the following steps:
1) A cross section is taken through the distal femur and proximal tibia relative to anatomical landmark.
2) An interpolated variable offset is applied to the cross section curve using a nominal value within the medial and lateral compartments and relative to anatomical landmarks.
3) Each point on the interpolated curve is examined for its relative distance across the joint space and limited to the tibia cross section.
4) The 3D points within distal femur mesh model are all examined for relative distance to each point on the offset curve.
5) Points within a specified threshold distance are translated in a direction normal to the underlying face with a magnitude relative to the reference curve.
6) Points within a specified blend distance are translated in a direction normal to the underlying face with a magnitude derived from a sinusoidal interpolation relative to the reference curve as shown in FIGS. 4(e) and 4(f).
7) The trochlea groove curve is identified by examining the geometry using a series of cross sections.
8) Steps 2-6 are applied to the distal femur.
9) Steps 2-8 are applied using 3 nominal offset values of 1 mm, 2 mm and 3 mm.

Figure 4B:
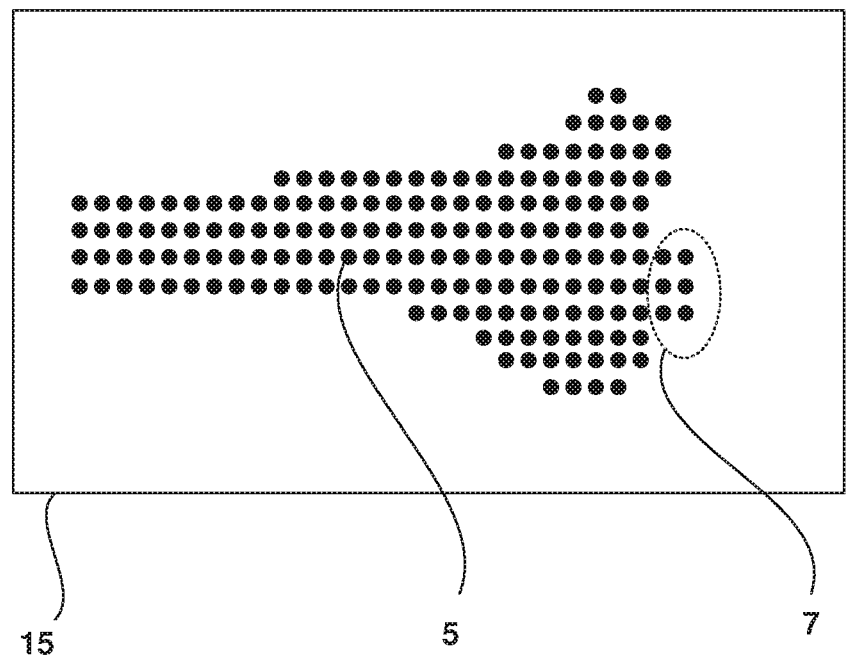
FIG. 4(b) illustrates a representation of spatial data indicative of the position of the anatomical feature and tool interface in FIG. 4(a)
Figure 4C:
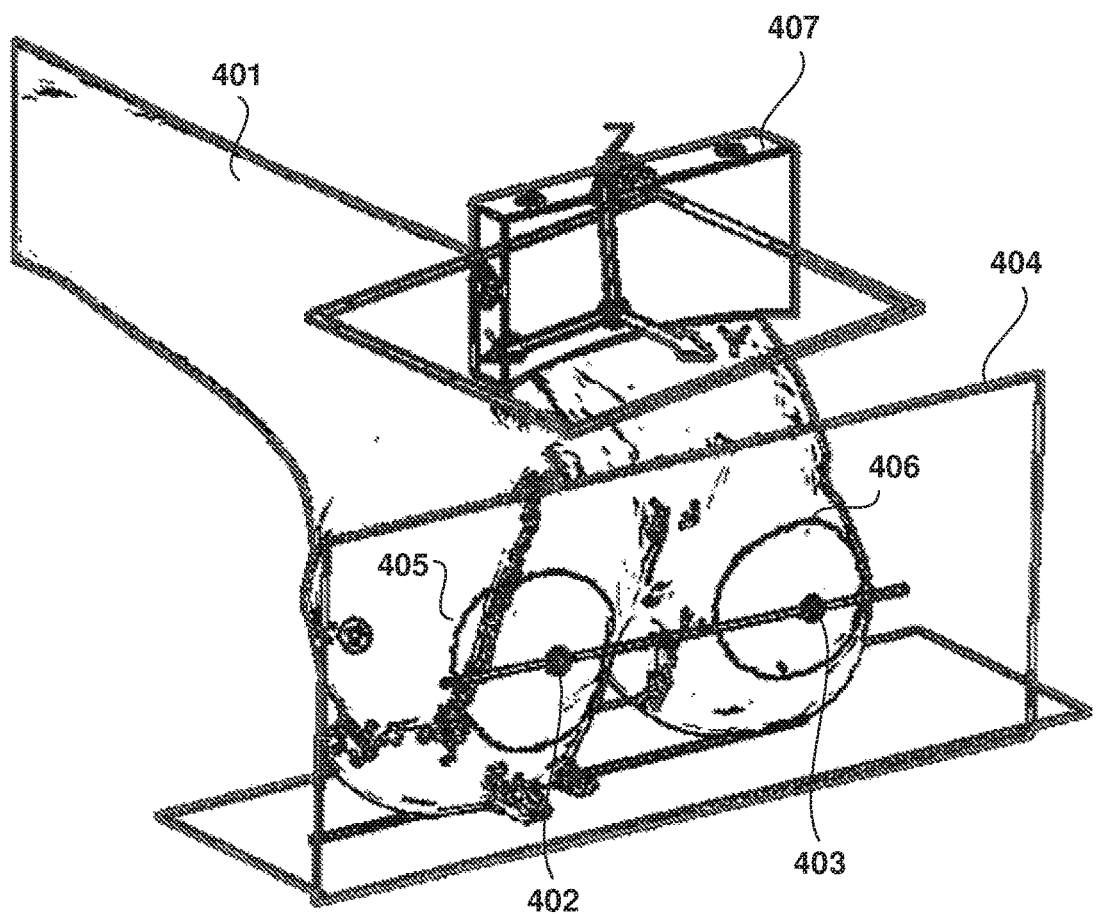
FIG. 4(c) illustrates a 3D mesh model.
Figure 4D:
FIG. 4(d) shows a graphical representation of tags within the distal femur.
Figure 4E:
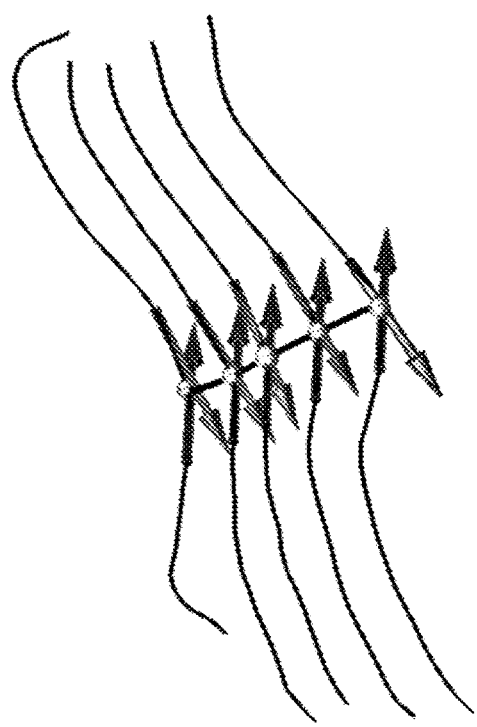
FIGS. 4(e) and 4(f) illustrate a translation of points.
Figure 4F:
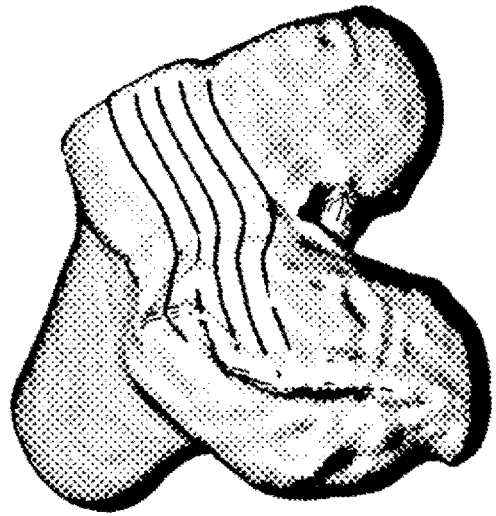
Figure 4I:
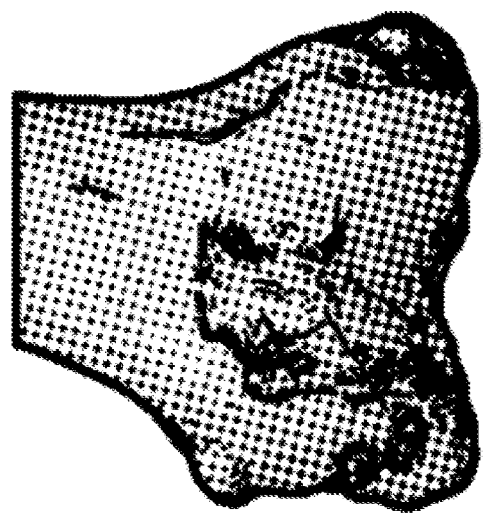
FIGS. 4(g), 4(h) and 4(i) illustrates the original, a joint space morph and troch morph model, respectively.
Figure 4H:
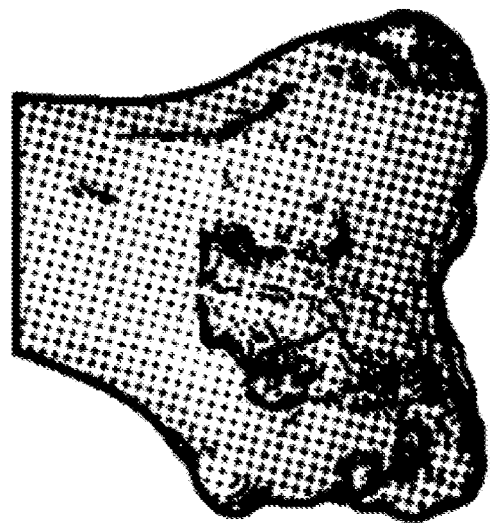
Figure 4G:
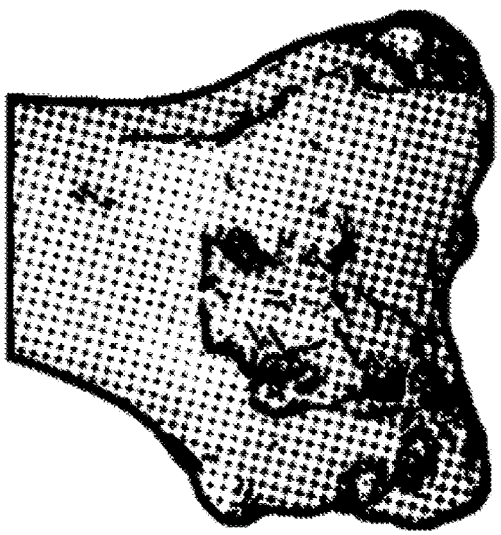

FIGS. 4(g), 4(h) and 4(i) illustrates the original, a joint space morph and troch morph model, respectively.

Figure 4J:
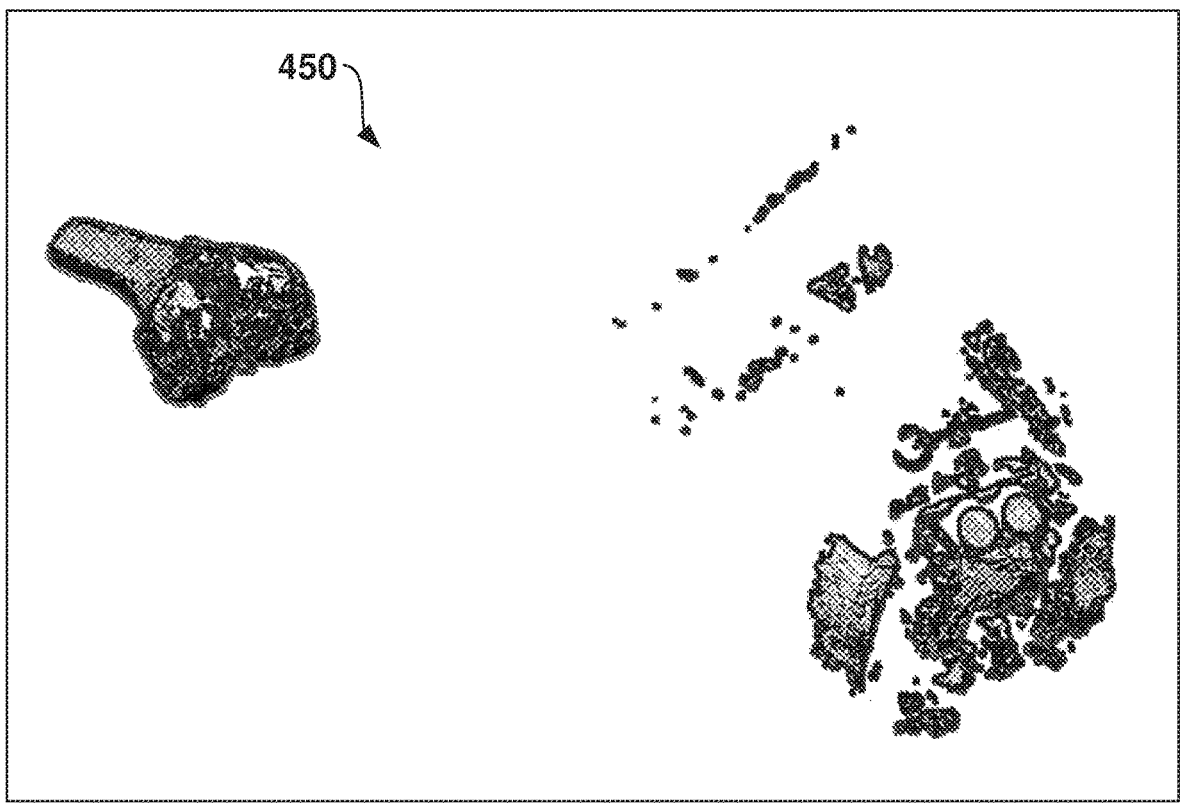
FIG. 4(j) illustrates an initial scan.
Figure 4K:
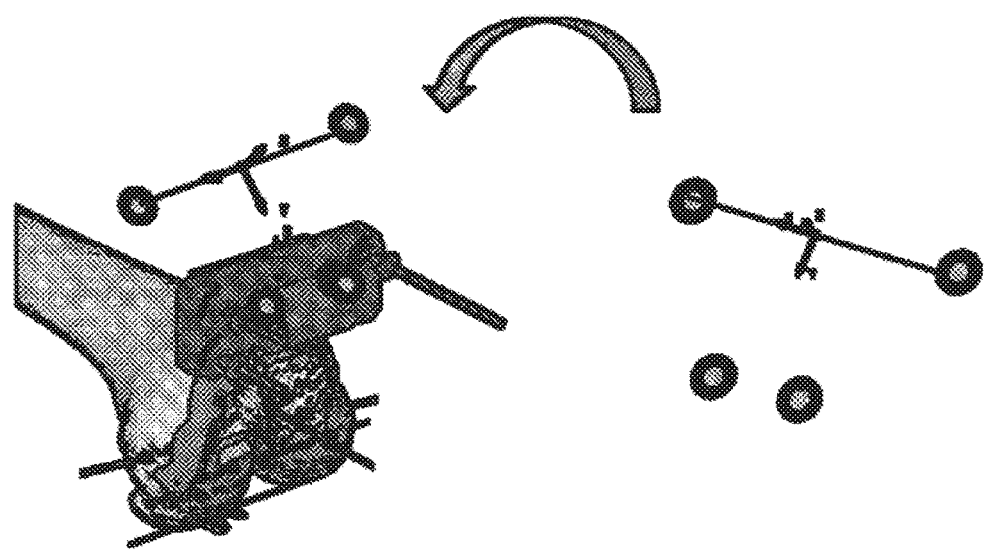
FIG. 4(k) illustrates a point on normal direction of each target.

After the morphing is performed, processor 102 performs the alignment process. FIG. 4(j) illustrates an initial scan 450 created within "camera space". The point on normal direction of each target is recorded relative to the same co-ordinate system of the scan as shown in FIG. 4(k).

FIGS. 4(l) and 4(m) illustrate how the scan and targets, respectively, are transformed relative to the default array position. FIG. 4(n) shows the 21,000 nodes of the scan while FIG. 4(o) shows the 3,500 nodes of the 3D mesh model. In this example none of the connect regions are filtered out and the scan is limited to a silhouette of the 3D segmented mesh relative to the co-ordinate system within the pre-operative plan.

Figure 4P:
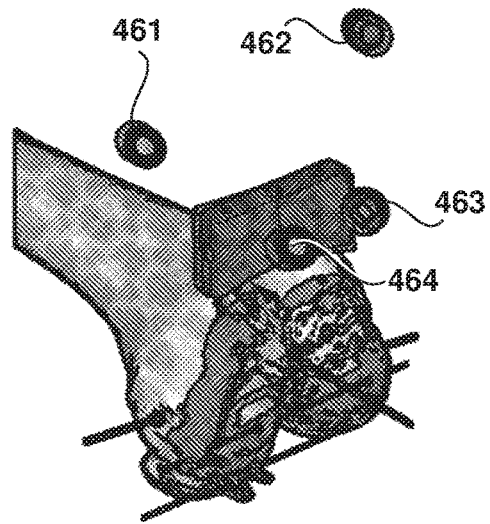
FIGS. 4(p) and 4(q) illustrate an iterative alignment process.
Figure 4Q:
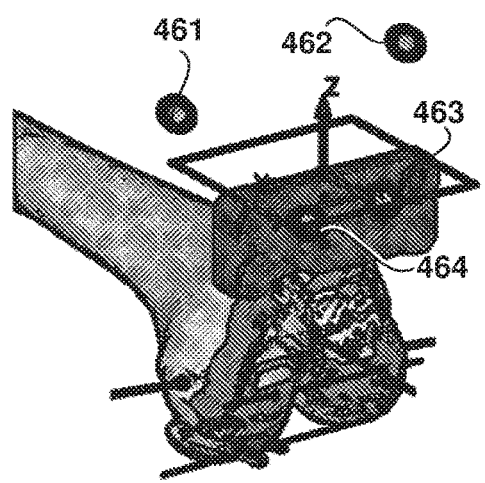

FIGS. 4(p) and 4(q) illustrate an iterative alignment process. It can be seen that it FIG. 4(p) there is some misalignment at points 461, 462, 463 and 464 while in FIG. 4(q) the alignment of those points is improved. The iterative alignment process is performed between cloned copies of the scan and each of the surrogate models. The iterative alignment process may stop iterating once a "best fit" based on mean deviation has been achieved.

Figure 4R:
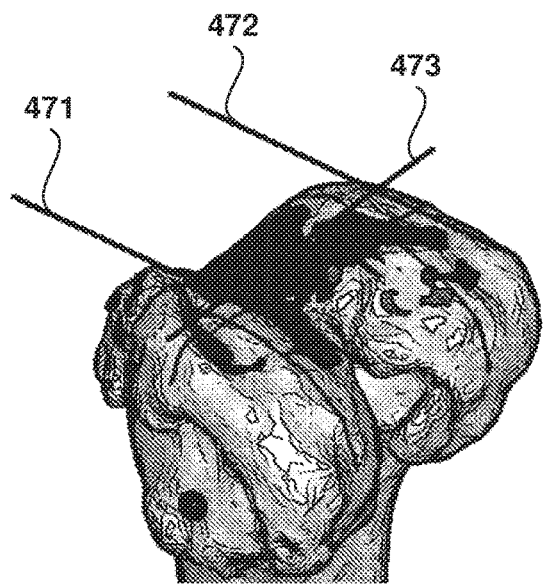
FIG. 4(r) illustrates a projection of points onto a bone surface.
Figure 4S:
FIG. 4(s) illustrates a distance of each projected point.

The alignment between each of the surrogate models and the 3D segmented mesh is analysed by processor 102 using the following process:
1) A normal vector is determined for each face within the scan mesh
2) The vector is intersected with the underlying 3D segmented mesh
3) The magnitude of the intersected vector is added to a deviation list.
4) Mean deviation, RMS error and Standard deviation are all calculated.
5) As shown in FIG. 4(r) a series of linear points along the medial lateral compartments 471, 472 and across the Trans Epicondyle reference line 473 are projected onto both the scan mesh and the 3D segmented mesh and the distance between each projected point is recorded as shown in FIG. 4(s).
6) A linear regression is performed between each of the deviation lists determine if there is a medial\lateral, anterior\posterior displacement.
7) The alignment with the lowest RMS error and smallest medial\lateral and anterior\posterior displacement is selected for reference tool alignment providing it is within a predetermine threshold. In one example the threshold is an RMS of less than 1 and a and a linear regression slope less than 0.5 degrees.

In FIG. 4(b) the representation is a two dimensional representation of points in a 3D point cloud. It is to be appreciated that the sensor system 9 may also provide sensor data indicative of a range of one or more of the points. Range information may also be used to assist feature extraction and/or determination of the respective positions of the anatomical feature 5 and tool interface 7 as described further below. In other words, the 3D point cloud generally comprises points that cover the entire viewing area including the theatre table, the floor or other equipment, such as lights. For illustrative purposes FIG. 4(b) comprises only those points that are within a small distance from the bone surface. For example, the processing device 13 may determine the maximum measured distance and the minimum measured distance in the point cloud. Processing device 13 may then step through the distances until the shape of the marker 71 can be detected using pattern matching. Processing device 13 may then use those points that are within a set distance, such as 10 cm, from the distance of the marker 71. These are the points that are shown in FIG. 8(b).

It is to be appreciated that the relative position of the anatomical feature 5 to the tool interface 7 may also be determined from the sensor data. Referring to FIG. 4(a), relative position 39 may be the distance and orientation between the tool interface 7 and a reference point 37 of the anatomical feature 5.

In the example above, spatial data is in the form of a 3D point cloud. Other forms of spatial data may include digital images (including stereoscopic images), position data on absolute positions of the anatomical feature 5 and tool interface 7, relative position of the anatomical feature 5 and the tool interface 7, etc. In turn, these may be represented in various coordinates systems, including those described above.

Importantly, the spatial data 15 provides information of the relative position 39 of the tool interface 7 and the anatomical feature 5 which can then be used to assist configuring the surgical tool 3 to the second desired spatial configuration discussed below.

Determining a First Desired Spatial Configuration of the Surgical Tool in Relation to the Tool Interface 220

The next step is to determine 220 a first desired spatial configuration 17 of the surgical tool 3 in relation to the tool interface 7 based on spatial data 15 and the second desired spatial configuration 19. An example will now be described with reference to FIG. 5 that shows a surgical tool 3 cutting into the anatomical feature 5.

The spatial data 15 may be used to derive the relative position 39 between the tool interface 7 and the reference point 37 of the anatomical feature 5. The second desired spatial configuration 19, including the cut line 21, may be defined by point 31 that is displaced 32 from the reference point 37. The processor may then apply known mathematical equations (such as trigonometric functions) to determine a first desired spatial configuration 17 of the surgical tool 3 (relative to the tool interface 7) that would configure the surgical tool 3 to be along cut line 21. The determined first desired spatial configuration 17 may be in the form of a vector 43 from the tool interface 43 to the surgical tool 3 and a first cutting angle 45 for the surgical tool 3.

The first desired spatial configuration 17 of the surgical tool 3 will configure the surgical tool 3 along the cut line 21. That is, configuring the surgical tool 3 in the same, or similar corresponding configuration, had the surgical tool been configured according to the second desired spatial configuration 19 (which would also configure the surgical tool 3 along cut line 21).

The dynamic model that is used to determine the second desired spatial configuration 19 may be based on a model coordinate system that can be arbitrary in relation to the anatomical feature. For example, the model coordinate system may have an x-axis that is identical to the longitudinal axis of the bone 43 and the origin of the coordinate system may be on an arbitrary point on that axis. The z-axis and y-axis are then orthogonal to the x-axis up to an arbitrary rotation around the x-axis. The second desired spatial configuration is then defined in relation to this model coordinate system with a desired relation to the anatomical feature 43. When the position of the tool interface 7 is determined, processing device 13 determines a transformation of the model coordinate system to the position of the tool interface 7. The same transformation can then be applied to the second desired spatial configuration to determine the first desired spatial configuration of the tool in relation to the tool interface. This may include multiplying the coordinates of the second spatial configuration by rotation matrices to rotate around respective coordinate axis:

$$R_x(\theta) = \begin{bmatrix} 1 & 0 & 0 \\ 0 & \cos\theta & -\sin\theta \\ 0 & \sin\theta & \cos\theta \end{bmatrix}$$

$$R_y(\theta) = \begin{bmatrix} \cos\theta & 0 & \sin\theta \\ 0 & 1 & 0 \\ -\sin\theta & 0 & \cos\theta \end{bmatrix}$$

$$R_z(\theta) = \begin{bmatrix} \cos\theta & -\sin\theta & 0 \\ \sin\theta & \cos\theta & 0 \\ 0 & 0 & 1 \end{bmatrix}$$

The system 1 may provide an output signal, via output port 12, to set the surgical tool 3 to the first spatial configuration 17. The tool interface 7 may be interfaced with the surgical tool apparatus 47 to allow the surgical tool apparatus 47 to have an accurate reference with respect to the tool interface 7. Thus the surgical tool 3 (via the surgical tool apparatus) can be accurately configured relative to the tool interface 7.

Figure 5:
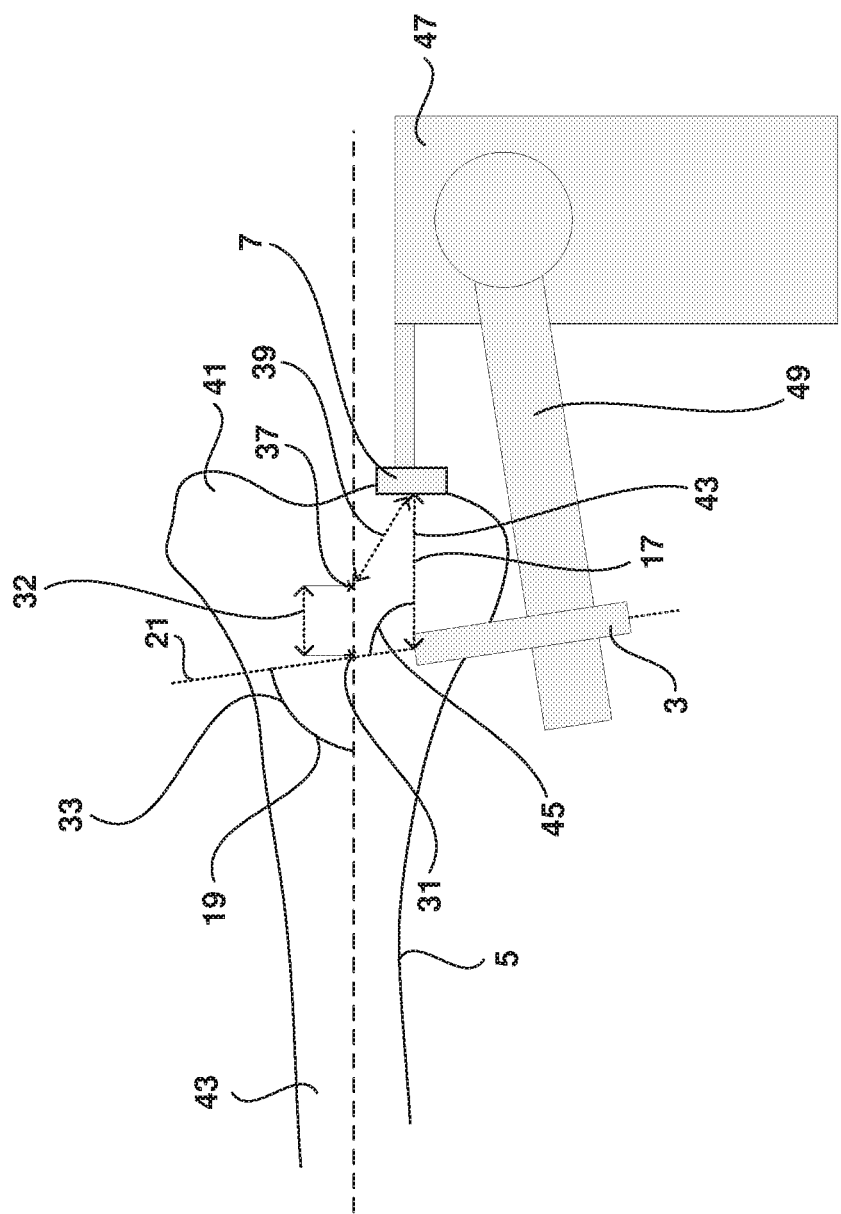
FIG. 5 illustrates a side view of the anatomical feature and a surgical tool during surgery.

In one example, the surgical tool apparatus 47 may include a robotic arm 49 having the surgical tool 3. The robotic arm 49 may include actuators to displace and orientate the surgical tool 3 in accordance with the output signal from the output port 12 such that the surgical tool is in the first spatial configuration 17 as illustrated in FIG. 5.

Alternatively, the surgical tool apparatus 47 may include adjustable mechanisms, such as guides and/or jigs to assist configuring the surgical tool 3 in relation to the tool interface 7. In one alternative, the output signal may provide visual indicia for the surgeon so that the surgeon can make appropriate adjustments to the surgical tool apparatus 47 to configure surgical tool 3.

Verifying Operation of the Surgical Tool and Implant

After the surgical tool 3 shapes the anatomical feature 5, such as making a cut along cut line 21 to provide the major portion 43, it may be desirable to verify the that the surface of the anatomical feature 5 is shaped to the desired shape.

FIG. 6 illustrates a major portion 43 of the anatomical feature 5 having a shaped end 51. The method may include subsequently performing another scan of the anatomical feature 5 with the sensor system 9, wherein sensor data may be sent to determine spatial data which in turn allows determination 230 of the result of applying the surgical tool 3. This may be similar to step 210, although the spatial data in this instance may not include position data of the tool interface 7 which may have been removed with the minor portion 41. In one example, a 3D point cloud of the major portion 43 may be used to determine the result of the shaped major portion. This result may be compared with the desired geometry of the anatomical feature to verify the result of applying the surgical tool 3. In one example, this may include determining the position of the shaped end 51. This may include determining a surface angle 53 relative to the reference axis 35.

The method may also include verifying the position of the implant 61 as shown in FIG. 7. After verifying the surfaces of the anatomical feature 5 is shaped as desired to receive the implant 61 the surgeon may then secure the implant 61, such as parts of a replacement joint, to the anatomical feature 5. The sensor system 9 may then perform a further scan, so that the processor may determine 240 a position of an implant in relation to the anatomical feature 5. This step is similar to the step of determining spatial data 210 described above, with the exception of determining the position of an implant 61 instead of the tool interface 7. In one example, this includes determining 240 the position of the implant 61 relative to the shaped end 51. This may include determining a surface angle 63 of the implant 61 relative to the reference axis 35. The surface angle 63 of the implant 61 may be compared to the surface angle 53 of the shaped end 51 to validate correct positioning of the implant 61.

Variation Using Markers

Figure 8A:
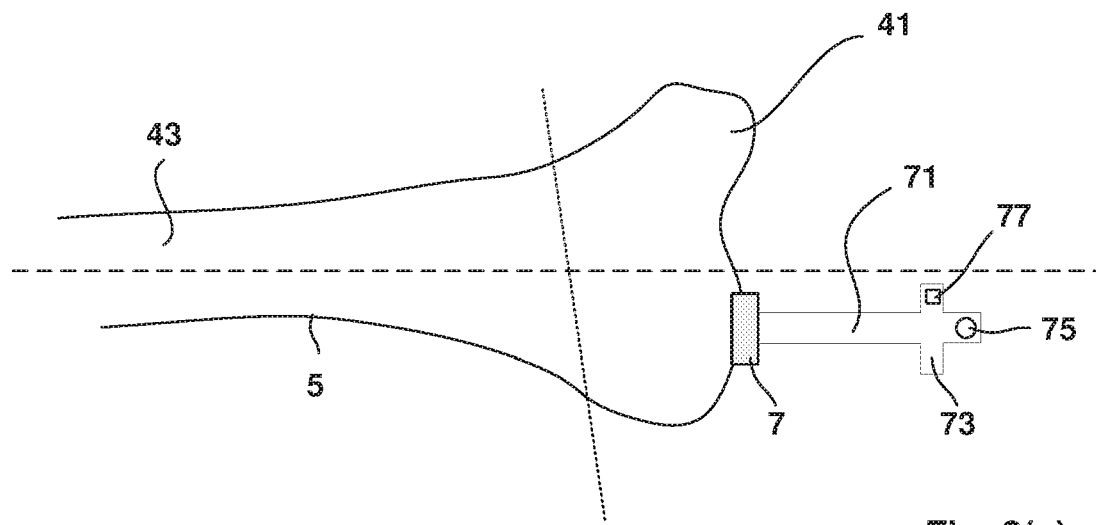
FIG. 8(a) illustrates a side view of an anatomical feature with a fixed tool interface and a marker.
Figure 8B:
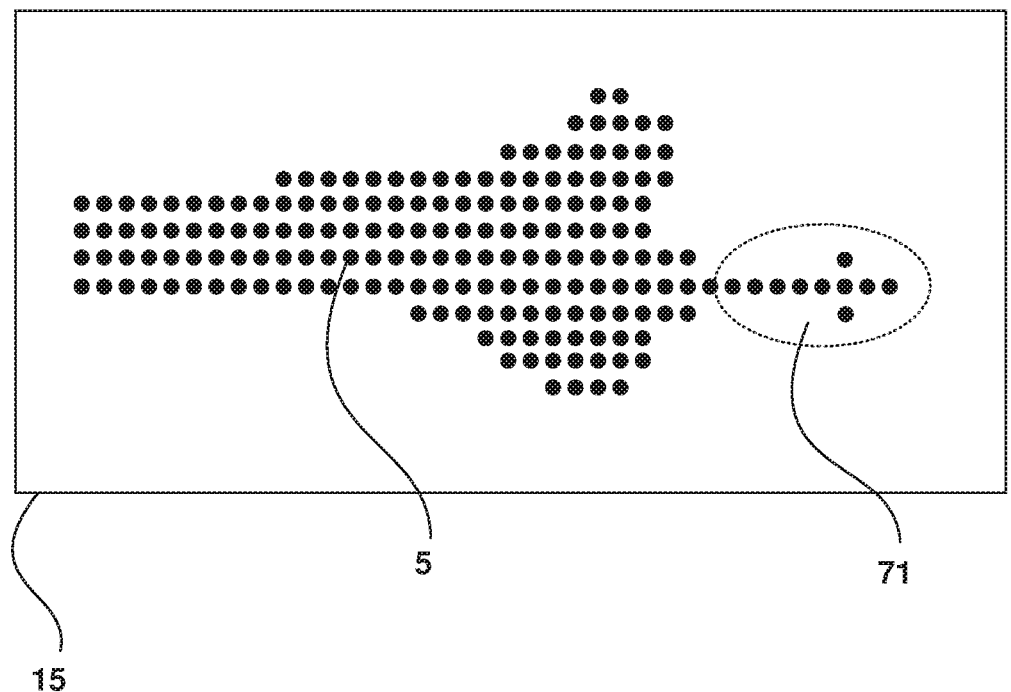
FIG. 8(b) illustrates a representation of spatial data indicative of the position of the anatomical feature and the marker in FIG. 8(a)
Figure 9:
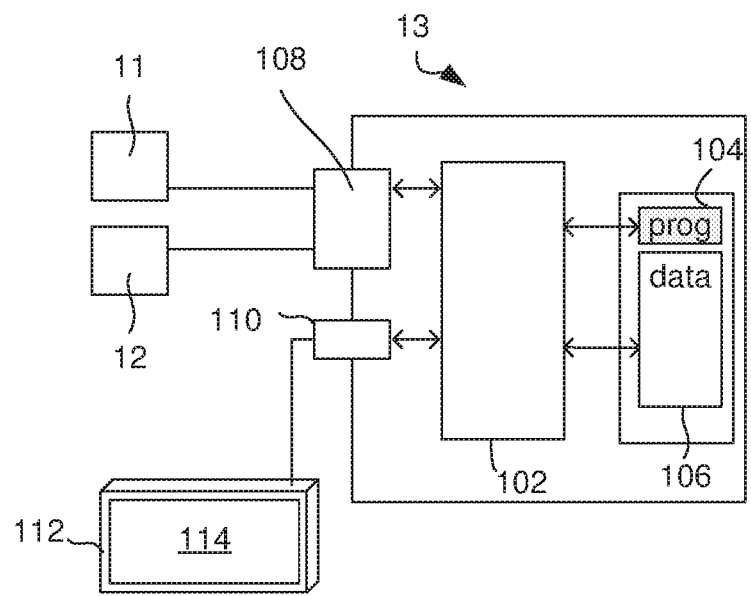
FIG. 9 illustrates a schematic of a processing device.

FIGS. 8(*a*) and 8(*b*) illustrate an alternative where a marker 71 is used to assist in determining the position of the tool interface 7.

The marker 71 may be constructed with material that can be detected by the sensor system 9. The marker 71 may include distinctive features that can assist detection. In the example illustrated in FIG. 8(*a*) a distinctive feature is the crucifix shape 73 of an end of the marker. In one alternative, the marker may include distinct features such as shapes or patterns, for example shape 75, 77 positioned at extremities of the crucifix 73. In some other alternatives, the marker 71 may be made of different types of materials to provide distinctive features, where one material may be easily contrast and differentiable to another type of material. Such distinctive features may assist in detection of the marker 71 as well as determining information such as position, including orientation of the marker 71. This may be enhanced by selectively placing distinctive features on the marker 71 such that detection of particular distinctive features by the sensor system 9 may allow the processor to determine a unique position, including orientation, of the marker 71.

The marker 71 may be a device that can be engaged with the tool interface 7. For example, the tool interface 7 may include a socket to receive a corresponding spigot of the marker 71. Alternative forms of engagement between the tool interface 7 and marker 71 may include dovetail joint, bayonet mount, T slot and key system, interference fit, etc. Since the relative position of the tool interface 7 and the marker 71 may be specified or predefined (such as from manufactured specifications), if the position of the marker 71 is determined, in a manner similar to step 210, then the position of the tool interface 7 can also be determined.

Similarly, a marker 71 may also be used during the step 240 of determining the position of an implant 61. In this case, the marker 71 may be interfaced with the implant 61 after which the sensor system 9 may scan for the anatomical feature 5 and marker 71 similar to step 240 described above.

Markers 71 may be advantageous in circumstances where the sensor system 9 has difficulties detecting the tool interface 7 or determining the position of the tool interface 7 is otherwise difficult. For example, the tool interface 7 may be small or outside a line-of-sight of the sensor system 9.

Hardware

The present disclosure may be applicable to a wide range of surgical applications. This may include orthopaedic applications, such as arthroplasty where anatomical features such as bone, cartilage and/or soft tissue constructs may need to be reshaped and/or removed. In one example, this may include joint replacement surgery including joints such as the knee, hip, shoulder and elbows. It is to be appreciated that systems and apparatus for performing such procedures may be modified and/or otherwise adapted with the presently disclosed method 200 and system 1.

The surgical tool 3 may include a bone-preparation tool, such as a tool for cutting, drilling, reaming, machining, shaving and fracturing. An example includes a powered reciprocating saw blade. The saw blade may be guided by the surgical tool apparatus 41 such as from a robotic arm 49 that is actuated based on output signals from the processing device 13. The surgical tool apparatus 41 may have a microcontroller that receives the output signals and, in turn, provides control signals to actuators of the robotic arm 49.

The sensor system 9 may include a variety of sensor types suitable for detecting the position of the anatomical feature 5 and the tool interface 7. In one example, the sensor system 9 includes a range finding device to provide sensor data, in the form of range finder data, to determine the range from the sensor system 9. The range finding device may determine, for multiple points, a distance of the anatomical feature 5 and tool interface 7 to the position of the sensor system. An example includes a laser range finding device, that includes a steerable laser source 9' to project laser light, at multiple points, towards the anatomical feature 5 and tool interface 7. The reflected light may be detected by a light sensor (such as a photo detector 9") and the time of flight of the light used to determine a respective distance. In other examples, the sensor system 9 may include one or more digital image sensors (e.g. digital cameras) to provide sensor data. In one example, a system of stereoscopic digital cameras may be used to provide sensor data that can provide data indicative of position of the anatomical feature and tool interface in captured images.

The tool interface 7 may be made of material suitable for surgery, such as 316 stainless steel and may contain a location feature for a pre-drilled hole, fixation pin holes and 3 geometrical features. Examples include the probe spheres by Bal-tec. The tool interface 7 may include a socket to receive a corresponding spigot of the surgical tool apparatus 47. It is to be appreciated various ways of interfacing components may be used. Examples may include engagement using a dovetail joint, bayonet mount, T slot and key system, interference fit, etc. The tool interface 7 may be fixed to the anatomical features 5 by fasteners including pins and screws, adhesives, etc. It is to be appreciated that other suitable methods of fixing the tool interface 7 that is suitable for surgery may be used.

Processing Device

Figure 2:
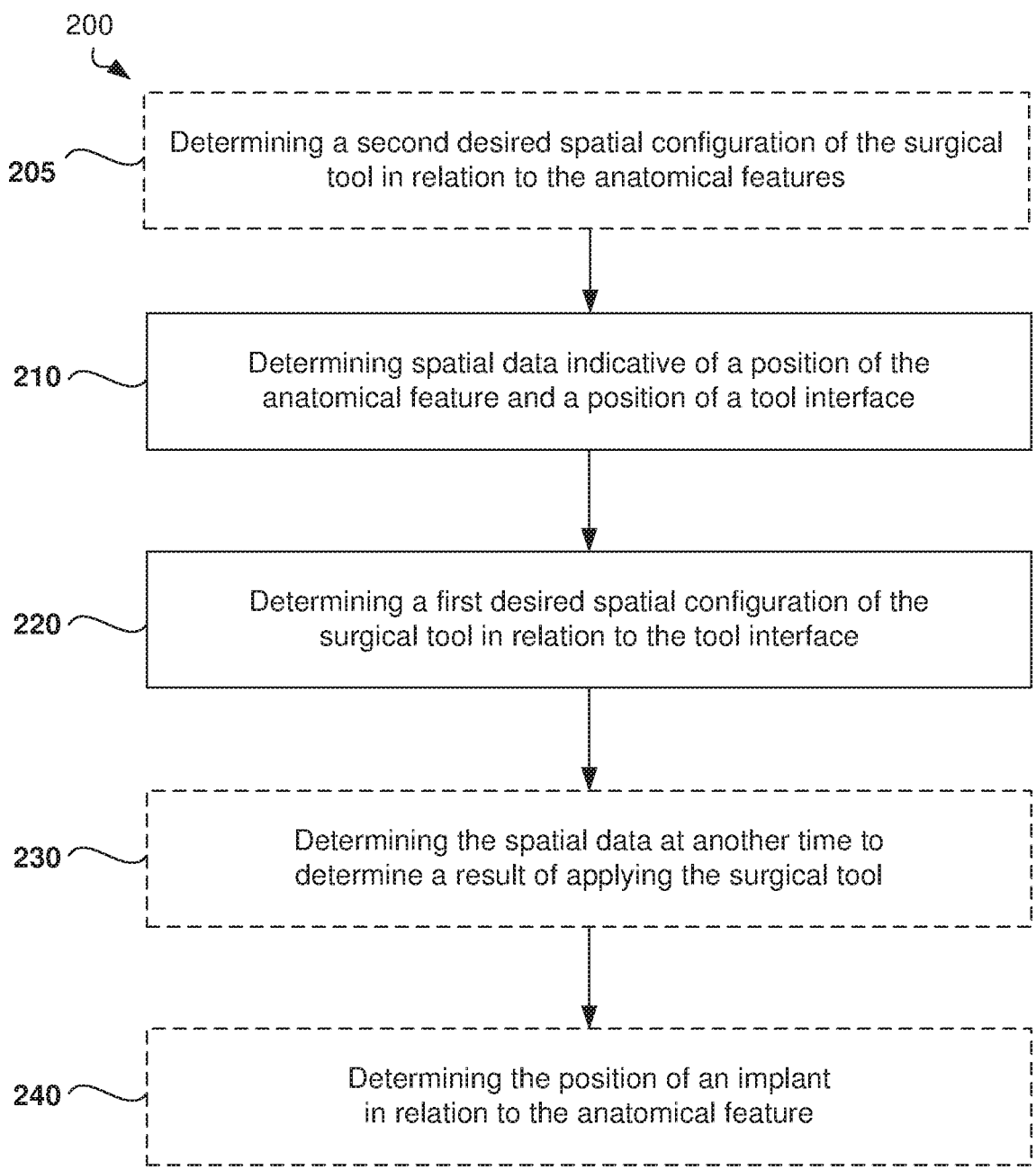
FIG. 2 is a flow diagram of a method for configuring a surgical tool in relation to an anatomical feature.

The processing device 13 includes a processor 102 connected to a program memory 104, a data memory 106, a communication port 108 and a user port 110. The program memory 104 is a non-transitory computer readable medium, such as a hard drive, a solid state disk or CD-ROM. Software, that is, an executable program stored on program memory 104 causes the processor 102 to perform the method in FIG. 2, that is, the method 200 of configuring a surgical tool 3 in relation to an anatomical feature 5.

The processor 102 may then store spatial data 15, sensor data (including range finder data), medical imaging data, data indicative of the first desired spatial configuration, data indicative of the second desired spatial configuration on data store 106, such as on RAM or a processor register. Processor 102 may also send the determined first desired spatial configuration, in the form of output signal via communication port 108 to an output port 12.

The processor 102 may receive data, such as sensor data, medical imaging data, data indicative of the first desired spatial configuration, data indicative of the second desired spatial configuration from data memory 106 as well as from the communications port 108 and the user port 110, which is connected to a display 112 that shows a visual representation 114 of the spatial data 15 to a user 116. In one example, the processor 102 receives sensor data from the sensor system 9 thorough the input port 11 and/or communications port 108.

Although communications port 108 and user port 110 are shown as distinct entities, it is to be understood that any kind of data port may be used to receive data, such as a network connection, a memory interface, a pin of the chip package of processor 102, or logical ports, such as IP sockets or parameters of functions stored on program memory 104 and executed by processor 102. These parameters may be stored on data memory 106 and may be handled by-value or by-reference, that is, as a pointer, in the source code.

The processor 102 may receive data through all these interfaces, which includes memory access of volatile memory, such as cache or RAM, or non-volatile memory, such as an optical disk drive, hard disk drive, storage server or cloud storage. The processing device 13 may further be implemented within a cloud computing environment, such as a managed group of interconnected servers hosting a dynamic number of virtual machines.

Example methods for conversion between quaternions and Euler angles is described in "Euler Angles, Quaternions and Transformation Matrices", NASA Working Relationships, Mission Planning and Analysis Division, July 1977, which is included herein by reference.

FIG. 10a illustrates example code for the determination of the rotation angle while FIG. 10b illustrates example code for creating a transformation from three spheres.

An example method for least squares fitting of data is described in: David Eberly, "Least Squares Fitting of Data", Geometric Tools LLC, Jul. 15, 1999.

FIG. 11 illustrates steps of a method for fitting a sphere to 3D Points. Given a set of points $[(x_i, y_i, z_i)]_{i=1}^m$, $m \geq 4$ fit them with a sphere $(x-a)^2+(y-b)^2+(z-c)^2=r^2$ where (a, b, c) is the sphere center and r is the sphere radius. An assumption of this algorithm is that not all the points are coplanar. The energy function to be minimized is expression 1102 where $L_i = \sqrt{(x_i-a)^2+(y_i-b)^2+(z_i-c)}$. Taking the partial derivative with respect to r results in expression 1104.

Setting equal to zero yields expression 1106. The next step is taking the partial derivative with respect to a to obtain expression 1108, taking the partial derivative with respect to b to obtain expression 1110 and taking the partial derivative with respect to c to obtain expression 1112.

Setting these three derivatives equal to zero yield expressions 1114, 1116 and 1118, respectively.

Replacing r by its equivalent from $\partial E/\partial r = 0$ and using $\partial L_i/\partial a = (a-x_i)/L_i$, $\partial L_i/\partial b = (b-x_i)/L_i$, $\partial L_i/\partial c = (c-x_i)/L_i$, processing device 13 can process the three nonlinear equations 1202, 1204 and 1206 in FIG. 12 where the parameters are according to expression 1208.

Processing device 13 can apply a fixed point iteration to solving these equations $a_0 = \bar{x}$, $b_0 = \bar{y}$, $c_0 = \bar{z}$ and $a_{i+1} = F(a_i, b_i, c_i)$, $b_{i+1} = G(a_i, b_i, c_i)$ $c_{i+1} = H(a_i, b_i, c_i)$.

An example method for sphere detection within the point cloud is provided in FIG. 13 and in: Anas Abuzaina, Mark S. Nixon, John N. Carter, "Sphere Detection in Kinect Point Clouds via the 3D Hough Transform", Computer Analysis of Images and Patterns Lecture Notes in Computer Science, Volume 8048, 2013, pp 290-297.

Processing device 13 may perform an iterative closes point method (ICP) as shown as pseudo-code in FIG. 14 and is described in: Ronen Gvili, "Iterative Closest Point", http://www.math.tau.ac.il/~dcor/Graphics/adv-slides/ICP-.ppt. FIG. 14 illustrates example code for iterative closest point calculation.

It will be appreciated by persons skilled in the art that numerous variations and/or modifications may be made to the specific embodiments without departing from the scope as defined in the claims.

It should be understood that the techniques of the present disclosure might be implemented using a variety of technologies. For example, the methods described herein may be implemented by a series of computer executable instructions residing on a suitable computer readable medium. Suitable computer readable media may include volatile (e.g. RAM) and/or non-volatile (e.g. ROM, disk) memory, carrier waves and transmission media. Exemplary carrier waves may take the form of electrical, electromagnetic or optical signals conveying digital data steams along a local network or a publically accessible network such as the internet.

It should also be understood that, unless specifically stated otherwise as apparent from the following discussion, it is appreciated that throughout the description, discussions utilizing terms such as "estimating" or "processing" or "computing" or "calculating", "optimizing" or "determining" or "displaying" or "maximising" or the like, refer to the action and processes of a computer system, or similar electronic computing device, that processes and transforms data represented as physical (electronic) quantities within the computer system's registers and memories into other data similarly represented as physical quantities within the computer system memories or registers or other such information storage, transmission or display devices.

The present embodiments are, therefore, to be considered in all respects as illustrative and not restrictive.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for configuring a bone preparation tool in relation to an anatomical feature of a bone, the method comprising:
   pointing a light source towards the bone to project light from the light source towards the bone;
   detecting light reflected by the bone;
   determining, based on the reflected light, spatial data indicative of a position of the anatomical feature and of a position of a reference feature that is fixed in relation to the anatomical feature;
   aligning an anatomical model with the spatial data; and
   determining a desired configuration angle of the bone preparation tool in relation to the reference feature based on;
   the spatial data, and
   a desired preparation angle of the bone in relation to the anatomical feature based on the anatomical model.

2. The method of claim 1, wherein determining the spatial data indicative of a position of the anatomical feature and of a position of a reference feature comprises determining spatial data indicative of a position of the anatomical feature and of a position of a tool interface.

3. The method of claim 1, wherein determining the spatial data indicative of a position of the anatomical feature and of a position of a reference feature comprises determining spatial data indicative of a position of the anatomical feature and of a position of a cartilage defect or a bone feature or both.

4. The method of claim 1, wherein the desired preparation angle of the bone in relation to the anatomical feature is based on a dynamic anatomical model.

5. The method of claim 4, wherein the desired preparation angle of the bone in relation to the anatomical feature is based on a dynamic simulation of the dynamic anatomical model.

6. The method of claim 4, wherein the anatomical feature is a model feature of the dynamic anatomical model.

7. The method of claim 1, wherein the anatomical model is a 3D mesh model.

8. The method of claim 1, wherein aligning the anatomical model with the spatial data is based on a default position of the reference feature.

9. The method of claim 1, wherein aligning the anatomical model with the spatial data comprises determining areas of the spatial data which are inaccurate and discarding the inaccurate areas from the alignment.

10. The method of claim 1, wherein aligning the anatomical model with the spatial data comprises determining areas of the spatial data which are highly accurate and aligning the anatomical model with the spatial data based on the highly accurate areas.

11. The method of claim 1, wherein aligning the anatomical model with the spatial data comprises morphing the anatomical model.

12. The method of claim 1, wherein the reference feature comprises a tool interface, and wherein determining spatial data indicative of the position of the reference feature comprises determining spatial data indicative of a position of a marker engaged with the tool interface.

13. The method of claim 1, wherein the reference feature comprises a tool interface, and wherein determining spatial data comprises determining spatial data that is indicative of the position of the anatomical feature relative to the tool interface.

14. The method of claim 1, wherein determining the spatial data comprises determining the spatial data based on range finder data.

15. The method of claim 14, wherein determining the spatial data comprises determining for multiple points a distance from a sensor position.

16. The method of claim 1, further comprising determining the desired preparation angle based on the anatomical model and medical imaging data, wherein the desired preparation angle comprises a desired geometry of the anatomical feature after applying the bone preparation tool.

17. The method of claim 1, further comprising generating an output signal to set the bone preparation tool to the desired configuration angle.

18. The method of claim 1, further comprising:
performing the step of determining the spatial data at another time to determine a result of applying the bone preparation tool.

19. The method of claim 18, wherein determining the result of applying the bone preparation tool comprises determining a position of an implant in relation to the anatomical feature.

20. The method of claim 18, wherein determining the result of applying the bone preparation tool comprises determining a position of a marker.

21. A non-transitory computer readable medium with program code stored thereon that, when executed by a computer, causes the computer to perform a set of actions including:
determining, based on light detected as having been reflected by a bone, spatial data indicative of a position of an anatomical feature and of a position of a reference feature that is fixed in relation to the anatomical feature;
aligning an anatomical model with the spatial data; and
determining a desired configuration angle of a bone preparation tool in relation to the reference feature based on;
the spatial data, and
a desired preparation angle of the bone in relation to the anatomical feature based on the anatomical model.

22. A system for configuring a bone preparation tool in relation to an anatomical feature of a bone, the system comprising:
a light source configured to be directed towards the bone to project light from the light source towards the bone;
a light sensor to detect light reflected by the bone;
a processor
to determine, based on the reflected light, spatial data indicative of a position of the anatomical feature and of a position of a reference feature that is fixed in relation to the anatomical feature;
to align an anatomical model with the spatial data; and
to determine a desired configuration angle of the bone preparation tool in relation to the reference feature based on the spatial data and a desired preparation angle of the bone in relation to the anatomical feature based on the anatomical model.

* * * * *